(12) United States Patent
Mamedov et al.

(10) Patent No.: US 8,551,443 B2
(45) Date of Patent: Oct. 8, 2013

(54) MODIFIED ZINC FERRITE CATALYST AND METHOD OF PREPARATION AND USE

(75) Inventors: Aghaddin Mamedov, Houston, TX (US); Shahid Shaikh, Houston, TX (US); Clark Rea, Houston, TX (US); Xiankuan Zhang, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 316 days.

(21) Appl. No.: 12/874,479

(22) Filed: Sep. 2, 2010

(65) Prior Publication Data

US 2012/0059208 A1 Mar. 8, 2012

(51) Int. Cl.
*C07C 15/00* (2006.01)

(52) U.S. Cl.
USPC ........................................ 423/594.1; 502/329

(58) Field of Classification Search
USPC .............. 502/303–355; 423/594.1; 585/625, 585/906
See application file for complete search history.

(56) References Cited

U.S. PATENT DOCUMENTS

| | | | |
|---|---|---|---|
| 3,450,787 A | 6/1969 | Kehl et al. | |
| 3,595,810 A | 7/1971 | Kehl | |
| 3,951,869 A | 4/1976 | Baker | |
| 3,960,767 A | 6/1976 | Christmann et al. | |
| 4,172,854 A | 10/1979 | Ellis et al. | |
| 4,332,972 A | 6/1982 | Christmann et al. | |
| 4,658,074 A | 4/1987 | Bajars et al. | |

FOREIGN PATENT DOCUMENTS

| | | |
|---|---|---|
| CN | 1034853 C | 5/1997 |
| CN | 1184705 A | 6/1998 |
| CN | 1088624 C | 8/2002 |
| EP | 2256101 A2 | 12/2010 |
| WO | WO2008/140213 A1 | 11/2008 |
| WO | WO2009/045002 A1 | 4/2009 |
| WO | WO2009/119975 A2 | 10/2009 |

OTHER PUBLICATIONS

R. J. Rennard et al., Oxidative Dehydrogenation of Butenes over Ferrite Catalysts, Journal of Catalysts, Jul. 17, 1970, pp. 282-293, vol. 21.
J.A. Toledo et al., Effect of Al3+ Introduction into Hydrothermally Prepared ZnFe2O4, Applied Catalysis A: General, May 2000, pp, 235-245, vol. 196, Issues 1-2.
A.R. West, Solid State Chemistry and Its Application, 1984, pp. 292-298.
International Search Report dated Oct. 13, 2011, pp. 1-5, for International Application No. PCT/US2011/049856.
Written Opinion of the International Searching Authority dated Oct. 13, 2011, pp. 1-6, for International Application No. PCT/US2011/049856.
International Preliminary Report on Patentability for PCT/US2011/049856 dated Mar. 14, 2013, pp. 1-7.

*Primary Examiner* — Steven Bos
(74) *Attorney, Agent, or Firm* — Grady K. Bergen; Gino C. Catena; Griggs Bergen LLP

(57) ABSTRACT

A catalyst for oxidative dehydrogenation of organic compounds is provided by forming a solution of catalyst precursor components comprised of $Fe^{+3}$ and $Zn^{+2}$ cations and at least one other modifier element cation in water to form an aqueous solution of the catalyst precursor components. The modifier element cation has a standard reduction potential of from greater than about $-2.87$ E° (V) to less than about $-0.036$ E° (V) with a valence of +2. A base is separately and simultaneously added to the aqueous solution in amounts to maintain the pH of the aqueous solution at a pH of from about 8.5 to about 9.5 as the catalyst precursor components. The catalyst precursor components are allowed to react and precipitate out of solution as a precipitate. The resulting precipitate is calcined to form a modified zinc ferrite catalyst compound.

20 Claims, No Drawings

MODIFIED ZINC FERRITE CATALYST AND METHOD OF PREPARATION AND USE

BACKGROUND

The present invention relates to oxidative dehydrogenation reactions and methods of preparing catalysts and catalysts used for such reactions.

DETAILED DESCRIPTION

Butadiene is a valuable commercial product that is primarily used in the preparation of synthetic rubbers, such as polybutadiene rubber and styrene butadiene rubber. It is also used as a component in the production of acrylonitrile-butadiene-styrene (ABS) plastic. Butadiene may be produced from butenes through dehydrogenation. Butenes are typically derived from cracking of long chain petroleum products found in crude oil, with the butenes eventually being separated through fractional distillation.

Zinc ferrite catalysts have been used for oxidative dehydrogenation of organic compounds, such as converting alkenes to alkadienes and butene to butadiene. By combining certain modifiers and using particular preparation techniques, zinc ferrite catalysts with increased conversion and/or selectivity for alkadienes when used in oxidative dehydrogenation reactions may be formed. The catalysts may also have increased stability.

It should be noted that in this description, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every amount within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific points, it is to be understood that inventors appreciate and understand that any and all data points within the range are to be considered to have been specified, and that the inventors have disclosed and enabled the entire range and all points within the range.

The zinc ferrite catalyst formed in accordance with the invention typically has a spinel crystalline structure. Spinels are a known class of minerals having the general formulation $A^{+2}B_2^{+3}O_4^{-2}$, wherein the cations A and B occupy some or all of octahedral and tetrahedral sites in the crystalline lattice. A and B are divalent and trivalent cations, respectively, including magnesium, zinc, iron, manganese, aluminum, chromium. A and B can be the same metal with different charges, such as $Fe_3O_4$ (as $Fe^{+2}Fe_2^{+3}O_4^{-2}$) or a divalent oxide system (Zn, Fe) $Fe_2O_4$. The spinel structure can be provided by providing the precursors in the appropriate stoichiometric ratios and in the appropriate oxidation states. The spinel structure for zinc ferrite can be represented by the basic formula $ZnFe_2O_4$. In practice, the relative amounts of the zinc and iron components may vary while still providing the basic spinel crystalline structure, with additional amounts of the iron oxide phase ($Fe_2O_3$) being mixed therein. In some cases an excess of $Fe_2O_3$ may be added to change the catalyst activity. It is known that the presence of excess $Fe_2O_3$ phase in addition to the zinc ferrite spinel increases the activity of catalyst. In some cases it may be necessary to add modifier elements to regulate the ratio of spinel and separate $Fe_2O_3$ phases due to the participation of different elements in octahedral and tetrahedral cells of the spinel structure. These additional elements prevent agglomerization of the active sites and also regulate the concentration of oxygen sites on the surface, thus regulating the selective reactions and preventing complete oxidation to carbon dioxide.

The zinc and iron precursors are those that ultimately provide zinc and iron oxides in the appropriate oxidation states and that may facilitate the reaction of these compounds to form the zinc ferrite compound. The zinc precursors are those that provide $Zn^{+2}$ cations and the iron precursors are those that provide $Fe^{+3}$ cations, which may be contained in an aqueous solution. The zinc and iron precursors may include their salts. In certain embodiments a mixture of oxides and salts of zinc and iron are used as the precursors, with a base, such as ammonium hydroxide ($NH_4OH$) being added separately, as will be described later on, to form their cation hydroxides. A suitable source of zinc and iron cations include their nitrates, hydroxides, hydrates, oxalates, carbonates, acetates, formats, halides, oxides, metallic forms (e.g. metallic iron), etc., which may be used alone or in combination with one another. A particularly well suited $Zn^{+2}$ cation source is zinc nitrate [$Zn(NO_3)_2$]. Another suitable source of $Zn^{+2}$ cations may include zinc chloride. The different zinc cation sources may each be used alone or in combination with one another. A particularly well suited source of $Fe^{+3}$ cations for the reaction is provided from ferrous nitrate [$Fe(NO_3)_3$]. Other suitable sources of iron cations may include iron chloride or iron metal, which may be used alone or in combination with one another. The iron metal may be in the form of a powder that may be mixed with the precipitate of the zinc or it can be precipitated together with the zinc or precipitated separately and then mixed with the zinc precipitate. The precursors may all be present in an acidic solution.

A modifier element is also used in forming the zinc ferrite catalyst in accordance with the present invention. The modifier may constitute a "mildly basic" element that facilitates weakening of the iron-oxygen bond of the ferrite compound and regulate the bond energy of the oxygen in the spinel structure. A catalyst with very low oxygen bond energy leads to an excessive level of oxidation, with the reaction ultimately resulting in the formation of carbon dioxide instead of the desirable intermediate reaction products. A catalyst with very high oxygen bond energy of the ferrite compound decreases the conversion in the catalyst reaction. Therefore, on one hand the catalyst should retain a balance with respect to the oxygen bond energy so that it retains a high conversion through the participation of oxygen to selective reaction sites. On the other hand, the oxygen should not be so easy to remove as to result in a high degree of oxidation. Therefore, modification of the oxygen sites is required.

The "mildly basic" modifier element may be further characterized in terms of its redox potential in the oxidation-reduction step. Those mildly basic modifiers may include those that have a 2+ valance and a standard reduction potential of from greater than about −2.87 E° (V) to less than about −0.036 E° (V) at 25° C. in an aqueous solution. The modifier element may include those Group 2A, 3A and 6A elements of the periodic table, as well as the lanthanides and the elements of tin (Sn), vanadium (V) and bismuth (Bi) and any other elements that can provide the catalyst oxygen sites that increase the oxygen capacity of the catalyst. Non-limiting examples of modifier elements include the elements of Mn, Mo, V, Bi, Sb, Cr, Ce, La, Sm, Ca, Mg, Co, Sn, Al, Ba and Sr. In certain embodiments, only one of the listed modifiers may be used, with the remaining listed modifier elements not being used for a particular catalyst. In some embodiments, only two or three of the listed modifier elements may be used in combination for a particular catalyst with the remaining modifier elements not being used. Within the scope of the invention, the prior listing of modifier elements should be read to include each one individually for a particular catalyst, with all the rest being excluded. Where two or three modifier elements are used in combination, these may include the combination of any two or three of the listed modifier elements for a particular catalyst, with all the remaining modifier elements being excluded. In certain embodiments, one or all of the elements of chromium (Cr), magnesium (Mg), cobalt (Co), aluminum (Al), tin (Sn), vanadium (V), bismuth (Bi), barium (Ba), calcium (Ca) and strontium (Sr) may be excluded as modifiers for a particular catalyst.

The modifier element may be provided as a precursor that provides the modifier element or elements as a cation in the appropriate oxidation state and that may facilitate the reaction of the modifier element(s) with the other compounds to form the modified zinc ferrite compound. The modifier element precursors are those that provide modifier element cations in an aqueous solution. The modifier element precursors may include their nitrates and/or other salts for preparation of an aqueous solution of the cations. Alternatively, the modifier elements can be added as hydroxides. In certain embodiments only the salts of the modifier elements are used as the precursors, with a base, such as ammonium hydroxide ($NH_4OH$) being added separately, as will be described later on, to form their cation hydroxides. A suitable source of the modifier element cations include their nitrates, hydroxides, hydrates, oxalates, carbonates, acetates, formats, halides, oxides, etc., which may be used alone or in combination with one another. Particularly well suited modifier element sources are the nitrate salts of the modifier elements. Other suitable sources of modifier element cations may include their chlorides and carbonates, which may be used alone or in combination with one another.

The modifier element may replace some of the zinc or iron in the zinc ferrite crystalline structure ultimately formed. The modifier element may be added during the synthesis of the catalyst and not in a subsequent treatment of a previously formed zinc ferrite catalyst compound. If the modifier element cation is more stable in the +2 oxidation state during synthesis it tends to replace zinc. If the modifier is more stable in the +3 or higher oxidation state it tends to replace iron and thus be incorporated in both the tetrahedral and octahedral sites of the spinel structure.

The modifier element may be used in an amount to provide from about 1 wt. % to about 15 wt. %, more particularly from about 1 wt. % to 8 wt. %, and still more particularly from about 1 wt. % to 5 wt. % of the modifier element(s) by total weight of the modified zinc ferrite catalyst compound. In certain embodiments, the modifier element(s) is used in an amount to provide from about 1.5 wt. % to about 2.5 wt. % of the modifier element by total weight of the modified zinc ferrite catalyst compound. In other embodiments the modifier elements are used in an amount to provide from less than about 2 wt. % of the modifier element by total weight of the modified zinc ferrite catalyst compound.

In the synthesis of the modified zinc ferrite compound, a base is added along with the zinc ferrite precursor components to water. Two separate solutions may be prepared, such as a base or $NH_4OH$ solution and one or more solutions of the catalyst precursor components as their cation nitrates or other salts. The solutions are mixed in appropriate stoichiometric quantities and at a pH level to facilitate the desired precipitation. This may be accomplished by adjusting the rate of addition of the components to the reaction solution. To facilitate simultaneous precipitation of Zn and Fe, a pH value in the range of from about 7.5 to about 10, more particularly from about 8.5 or 8.6 to about 9.5 may be used. In some embodiments, the pH may range from between about 8.5, 8.6, 8.7, 8.8, 8.9, 9.0, 9.1, 9.2, 9.3 or 9.4 to about 9.5.

In certain embodiments, a two step precipitation method may be used wherein the Zn and Fe precursors are first added and precipitated from solution by the controlled addition of a base without any modifier element being first added to the solution. Once the Zn and Fe components are precipitated, the modifier elements may be added to the reaction solution with the controlled addition of the base to precipitate the modifier elements. In other embodiments, a single step precipitation method is used with the Zn, Fe and modifier element components all being added in solution and precipitated out simultaneously by the controlled addition of the base.

The base may be any base that facilitates effective co-precipitation of the modified zinc ferrite compounds and the soluble ions. The $NH_4NO_3$ or $NaNO_3$ formed during precipitation can be subsequently removed from the mix medium by de-ionized water wash followed by filtration, after the precipitate has been formed. Non-limiting examples of suitable bases include ammonium hydroxide, ammonium carbonate, ammonium bicarbonate, sodium hydroxide and potassium hydroxide. Where NaOH is used as precipitation agent with chloride salts of the catalyst precursor elements, such as $FeCl_3$, $ZnCl_2$ and the chlorides of additional elements, the dissolved sodium chloride may be removed from the mixture of precipitate with de-ionized water. Multiple washings (e.g. 2-3 times) of the precipitate with water may facilitate removal of ions and other contaminates. The use of $NH_4OH$ as the base solution facilitates the easy removal of ammonium ions ($NH_4^+$) in comparison with sodium and potassium ions.

In certain embodiments, the base is separately and simultaneously admixed with the zinc, ferrite and modifier element precursor components to water to form an aqueous solution of the precursor reactants wherein the pH value of the solution is maintained at from about 8.5 or 8.6 to about 9.5 during the course of the reaction. This causes the hydroxides of the zinc, iron and modifier elements to co-precipitate out of the solution. Usually, co-precipitation is carried out by drop-wise or controlled addition of the base to the solution of catalyst precursor elements so that there is a continuous formation of precipitate as the base is added. All the precursor elements may be dissolved in water in advance of the addition of the base. The pH value of the precursor salt solution prior to the addition of the base and before precipitation may be around 0.8 to about 1. Initially, with the addition of the base, the pH value slowly increases until the desired pH level is reached. This is typically between about 8.5, 8.6, 8.7, 8.8, 8.9, 9.0, 9.1, 9.2, 9.3 or 9.4 to about 9.5. The pH value of the solution tends to change during the precipitation. Changes in the pH level may affect the size of the precipitate particles and result in non-uniform precipitation. Therefore, the rate of the addition of the base may be controlled to maintain the desired pH level. In certain embodiments, the pH may be maintained to from about 9.4 to about 9.5 by the controlled addition of the base throughout the precipitation. It has been discovered that the separate and simultaneous addition of the base with the various modified zinc ferrite catalyst precursors allows the precipitation of different elements having different $K_{sp}$ values (solubility equilibrium constant). Because of their higher solubility, some of the modifiers, elements such as Ca, Mg. Co, etc., can be lost during preparation.

The reaction is typically carried out at a temperature of from about 60° C. to about 95° C. Continuous or non-continuous mixing may also be used to facilitate the reaction of the various components.

In certain embodiments, a catalyst template is employed. The catalyst template may be a sesbania compound or other sugar compound. The sesbania compound may be in the form of a powder formed from sesbania seeds. Sesbania seeds contain high molecular weight hydrocolloidal polysaccharides composed of galactan and mannan units connected through glycoside linkages with a D-galactose/D-mannose ratio of approximately 2:1. The sesbania may be prepared from seeds that are ground into small particles, such as 60 mesh or less. The sesbania powder is prepared in advance and added to in the solution to which the zinc, iron and modifier element precursors and base are added. The sesbania or other template may be used in an amount of from about 0.005 g to about 0.1 g sesbania per gram of Fe by weight. The sesbania or organic template is subsequently oxidized to $CO_2$ and burned out of the catalyst.

After co-precipitation of the zinc, iron and modifier elements from solution in the form of hydroxides, incorporated with or without the sesbania or other template, the produced precipitate may be filtered and washed. Water (e.g. deionized water) is typically used as a washing liquid. The amount of water used during washing should be sufficient to remove unreacted components, such as nitrates, such as $NH_4NO_3$, and other residue, from the precipitated compounds. If NaOH is used as the base to precipitate the various compounds, the washing will facilitate removal of the formed $NaNO_3$. The amount of water used may be in the range of from about 30 to 50 g water per gram of precipitate. The water for washing may be divided into two, three or more parts wherein the precipitate is washed in separate washings with each part. Sufficient results have been achieved using three washings with 40 g water per gram of precipitate. The color of washed solution may show the remaining ions that are not precipitated from the salts. For other elements, such as cobalt, some amount of the cobalt salt may remain in solution, which gives a reddish color to the solution. Sufficient washing may therefore be evidenced by a reduction or change in the coloring of the washed precipitate.

The filtered and washed catalyst precipitate is then dried. Heating of the filtered precipitate to temperatures of from about 25° C. or more, from about 70° C. to about 100° C. or 150° C. or more suitable in most instances to facilitate drying. The filtered precipitate may also be agitated during this step to ensure uniform drying. Drying times are typically from about 10 to about 12 hours or more, although drying times may be varied.

After drying, the co-precipitated components are calcined. Calcining is conducted in the presence of oxygen, such as pure oxygen, air, oxygen enriched air or a mixture of oxygen and other gases. The calcination temperatures typically range from about 300° C. to about 650° C. Calcination times typically range from about 5 hrs to 24 hours or more. Examples of suitable calcination temperatures and times may be from about 600 to about 650° C. for 8 to 12 hours. At lower temperatures calcination times may be longer. Thus, at a calcination temperature of from about 400° C. to about 650° C. a suitable calcination time may be from 10 to 24 hours. During calcination, the hydroxide components are converted to oxides and are converted to the final crystalline structure of the modified zinc ferrite catalyst structure. As discussed earlier, any sesbania or other organic template used is typically consumed during the calcination step. The final calcined catalyst will have a primarily spinel crystal structure.

After calcining, the resulting modified zinc ferrite may be optionally bound with a binder. The binder materials may include inorganic oxide materials, such as alumina, clay and silica materials. The binder may be used to provide a desired shape to the catalyst, for example, $\frac{1}{16}$-inch cylindrical shaped extruded catalyst. The bound catalyst may contain from about 1 wt % to about 30 wt % of binder material by total weight of the catalyst. In some applications the binder may be present in an amount of from about 1 wt % to about 15 wt % binder by total weight of catalyst.

The modified zinc ferrite catalyst produced in accordance with the described method may have a brown color which corresponds to the color of $Fe_2O_3$ oxide, which exists in the catalyst in an excess amount. The catalyst having this color is mechanically hard, which is due to the properties of $Fe_2O_3$. If the catalyst during preparation has a black color it is typically very soft and may have a low activity and selectivity. This property is related to the formation of $Fe_3O_4$ instead of $Fe_2O_3$ during calcination. If the catalyst is not washed well the remaining $NH_4$ ion, during calcination, result in the formation of excessive $Fe_3O_4$, which results in lower catalyst activity. Therefore, the washing of catalyst may have an impact on the final catalyst performance.

The formed modified zinc ferrite catalyst has particular application for use in oxidative dehydrogenation reactions of organic compounds. In particular, the catalyst has application for use in oxidative dehydrogenation reactions for converting alkenes to alkadienes, and more particularly for converting butenes to butadiene. While the following description is directed primarily to the conversion of butenes to butadiene, it should be apparent to those skilled in the art that it has application to the conversion of other alkenes to alkadienes, as well as other oxidative dehydrogenation reactions, all of which are intended to fall within the scope of the invention.

In converting butenes to butadienes using the formed catalyst, the modified zinc ferrite catalyst is contacted with an appropriate feed of butene and oxygen gas under suitable reaction conditions to carry out the oxidative dehydrogenation of butene to form butadiene. The oxygen may be pure oxygen gas, air or oxygen enriched air, or a mixture of oxygen with other non-reactive gases, such as nitrogen, carbon dioxide, etc. The oxygen may be used in an amount to provide an $O_2$ to butene or other alkene feed of from about 0.4 to about 0.8, more particularly from about 0.5 to about 0.7. The alkene feed may be diluted with methane in a methane/alkene molar ratio of about 0.5:1 to about 2:1. In certain embodiments, a methane/alkene molar ratio of about 1:1 may be used.

In certain embodiments, water or steam may also be introduced into the reactor as cofeed along with the $HC/O_2$ feed. Water may be used in a water-to-alkene feed mole ratio of from about 6:1 to about 15:1. In certain embodiments, the water/alkene feed mole ratio may range from about 8:1 to about 12:1. The water or steam may be combined with HC and/or $O_2$ feed prior to introduction into the reactor or it may be introduced separately into the reactor. Mixing of the various components in the proper amounts introduced into the reactor may be carried out by the use of mass flow controllers.

The reaction may be carried out in a variety of different reactors that are commonly used for carrying out oxidative dehydrogenation reactions for hydrocarbons. Single or multiple reactors in parallel may be suitable for carrying out the oxidative dehydrogenation reaction or reactions. The reactor used for the reaction may be a fixed bed or a fluidized bed reactor. The reaction pressure may vary, but is typically carried out at atmospheric pressure. Reaction temperatures may vary, but typically range from about 300 to about 500° C., more particularly from about 300 to about 400° C., and still more particularly from about 320° C. or 340° C. to about 360° C., 370° C. or 380° C. Preheating of the reactor to the reaction temperature may be carried out by introducing heated nitrogen into the reactor. Once the reaction temperature is reached, the reactant feed may then be introduced into the reactor. Once the reaction is started, depending upon the activity of the catalyst, the set point temperature of the reactor may be adjusted. The oxidative dehydrogenation reaction is exothermic so that heat is produced during the reaction. If the catalyst is very active, a large amount of heat will be produced and the set point temperature may be reduced to maintain the desired reaction conditions.

Using the modified zinc ferrite catalyst provides a more stable catalyst with higher activity and selectivity compared to the same catalyst without such modification.

The following examples better serve to illustrate the invention.

EXAMPLES

Example 1

Comparative Catalyst

A zinc ferrite catalyst was prepared without the use of any modifier element. The catalyst was prepared by using 99.8 g $Fe(NO_3)_3 \cdot 9H_2O$ and 32.1 g $Zn(NO_3)_2 \cdot 6H_2O$, which were dissolved in 500 ml of deionized water with stirring at room temperature. To this solution was added a 20 wt. % aqueous $NH_4OH$ solution by drop wise addition until precipitation was complete. The amount of $NH_4OH$ solution needed for complete precipitation was 162 ml. Prior to addition of $NH_4OH$, the pH of the solution was 0.8. As $NH_4OH$ was added, the pH started to increase. When the full 162 ml $NH_4OH$ was added the final pH of the solution after precipitation was 9.2-9.4.

After precipitation, the temperature of the precipitate was increased to 75-80° C. After reaching this temperature, the heating was discontinued and the precipitate was allowed to cool to 33° C. At 33° C. the precipitate was filtered and then washed twice with 500 ml of deionized (1000 ml total). After washing, the precipitate was dried at 120° C. for 4 hours. The precipitate was then calcined at 250° C. for 10 hours and then the calcining temperature was increased to 650° C. for 10 hours. After calcination, the resulting catalyst was cooled, crushed and screened to provide 20-50 mesh size catalyst particles. The final catalyst had 17 wt. % Zn and 55 wt. % Fe.

Approximately 9 g (density 1.8) of the formed catalyst was used in the oxidative dehydrogenation of butene to butadiene in a fixed bed reactor at a space velocity 342 $h^{-1}$, an $O_2$/butene molar ratio of 0.65 and $H_2O/C_4$ ratio of 10. The molar feed composition was kept constant at $C_4H_8:CH_4:O_2:H_2O=1:1:0.65:10$. The reactor was initially heated in nitrogen flow to a temperature of 330° C. before the reactant components were added. Because the reaction is exothermic, the reaction temperature rapidly increased. During the reaction the temperature was maintained between about 340-380° C. The results are presented in Table 1 below. As can be seen from Table 1, the catalyst was not stable and the activity dropped significantly after 5 days.

TABLE 1

| Time on Stream (Days) | Butene Conversion, (%) | Selectivity to Butadiene (%) | Catalyst Bed Temperature (° C.) |
|---|---|---|---|
| 1 | 68.5 | 93.6 | 365 |
| 4 | 65.8 | 93.5 | 358 |
| 5 | 54.5 | 93.2 | 340 |

Example 2

Comparative Catalyst

A Zn—Fe—Co—Mg—Ca modified catalyst was prepared by precipitation of a catalyst precursor mixture of nitrate salts of Zn, Fe, Mg, Ca and Co by addition of a $NH_4OH$ solution (20 wt. %). The catalyst was prepared by using 99.8 g $Fe(NO_3)_3 \cdot 9H_2O$ salt; 32.1 g $Zn(NO_3)_2 \cdot 6H_2O$; 1.5 g $Ca(NO_3)_2 \cdot 4H_2O$; 3.0 g $Co(NO_3)_3 \cdot 6H_2O$ and 1.6 g $Mg(NO_3)_2 \cdot 6H_2O$, which were dissolved in 500 ml of deionized water with stirring at room temperature. To this solution was added a 20 wt. % aqueous $NH_4OH$ solution by drop wise addition until precipitation was complete. The amount of the $NH_4OH$ solution needed for complete precipitation was 162 ml. Prior to addition of $NH_4OH$, the pH of the solution was 0.8. As $NH_4OH$ was added, the pH started to increase. When the full 162 ml $NH_4OH$ was added the final pH of the solution after precipitation was 9.2-9.4.

After precipitation, the temperature of the precipitate was increased to 75-80° C. After reaching this temperature, the heating was discontinued and the precipitate was allowed to cool to 33° C. At 33° C. the precipitate was filtered and then washed twice with 500 ml of deionized water (1000 ml total). After washing, the precipitate was dried at 120° C. for 4 hours. The precipitate was then calcined at 250° C. for 10 hours and then the calcining temperature was increased to 650° C. for 10 hours. After calcination, the resulting catalyst was cooled, crushed and screened to provide 20-50 mesh size catalyst particles. The final catalyst had 9.93 wt. % Zn, 57.44 wt. % Fe, 0.04 wt. % Ca, 1.24 wt. % Co and 0.1 wt. % Mg.

Approximately 9 g of the formed catalyst was used in the oxidative dehydrogenation of butene to butadiene in a fixed bed reactor at a space velocity 342 $h^{-1}$, an $O_2$/butene molar ratio of 0.65 and $H_2O/C_4$ ratio of 10. The feed composition was held constant at $C_4H_8:CH_4:O_2:H_2O=1:1:0.65:10$. The reactor was initially heated in nitrogen flow to a temperature of 330° C. before the reactant components were added. During the reaction, the temperature was maintained at 360° C. The reaction temperature was 360° C. The results are presented in Table 2 below.

TABLE 2

| Time on Stream (Days) | Butene Conversion, (%) | Selectivity to Butadiene (%) | Catalyst Bed Temperature (° C.) |
|---|---|---|---|
| 1 | 17.0 | 42.6 | 360 |
| 2 | 16.1 | 40.6 | 360 |

Example 3

Comparative Catalyst

A Zn—Fe—Co—Mg—Ca modified catalyst was prepared by precipitation of a catalyst precursor mixture of nitrate salts of Zn, Fe, Mg, Ca and Co by addition of a $NH_4OH$ solution (20 wt. %) to the aqueous solution of these components in the presence of sesbania. The catalyst was prepared by using 99.8 g $Fe(NO_3)_3 \cdot 9H_2O$; 32.1 g $Zn(NO_3)_2 \cdot 6H_2O$; 1.5 g $Ca(NO_3)_2 \cdot 4H_2O$; 3.0 g $Co(NO_3)_3 \cdot 6H_2O$ and 1.6 g $Mg(NO_3)_2$, which were dissolved in 500 ml of deionized water with stirring at room temperature. Sesbania powder having a particle size of less than 60 mesh was also added to the solution and used in an amount of 0.36% wt in relation to the final catalyst (22 g). To this solution was added a 20 wt. % $NH_4OH$ solution by drop wise addition until precipitation was complete. Prior to addition of $NH_4OH$, the pH of the solution was 0.8. As $NH_4OH$ was added, the pH started to increase. The amount of $NH_4OH$ needed for complete precipitation was 162 ml. When the addition of the 162 ml $NH_4OH$ was completed the final pH of the solution after precipitation was 9.2-9.4.

After precipitation, the temperature of the precipitate was increased to 75-80° C. After reaching this temperature, the heating was discontinued and the precipitate was allowed to cool to 33° C. At 33° C. the precipitate was filtered and then washed twice with 500 ml of deionized (1000 ml total). After washing, the precipitate was dried at 120° C. for 4 hours. The precipitate was then calcined at 250° C. for 10 hours and then the calcining temperature was increased to 650° C. for 10 hours. After calcination, the resulting catalyst was cooled, crushed and screened to provide 20-50 mesh size catalyst particles. The final catalyst had 13.44 wt. % Zn, 54.45 wt. % Fe, 0.21 wt. % Ca, 2.50 wt. % Co and 0.08 wt. % Mg.

Approximately 9 g of the formed catalyst was used in the oxidative dehydrogenation of butene to butadiene in a fixed bed reactor at a space velocity 342 $h^{-1}$, an $O_2$/butene molar ratio of 0.65 and $H_2O/C_4$ ratio of 10. The molar feed composition was held constant at $C_4H_8:CH_4:O_2:H_2O=1:1:0.65:10$. The reactor was initially heated in nitrogen flow to a temperature of 330° C. before the reactant components were added. The reaction temperature was 363° C. The results are presented in Table 3 below.

TABLE 3

| Time on Stream (Days) | Butene Conversion, (%) | Selectivity to Butadiene (%) | Catalyst Bed Temperature (° C.) |
|---|---|---|---|
| 1 | 70.4 | 93.3 | 363 |
| 2 | 69.4 | 93.0 | 363 |
| 4 | 68.7 | 93.4 | 363 |

Example 4

A Zn—Fe—Co—Mg—Ca modified catalyst in this example was prepared by stoichiometric precipitation of a catalyst precursor mixture of nitrate salts of Zn, Fe, Mg, Ca and Co with a $NH_4OH$ solution (20 wt. %) without the use of sesbania. In this example, the mixture of precursor salts and $NH_4OH$ were added in stoichiometric amounts to water. The $NH_4OH$ was added at a controlled rate to maintain a fixed pH of about 9.4, with precipitate formation growing uniformly with the addition of the $NH_4OH$ and the precursor. The precursor was prepared by dissolving of 99.8 g $Fe(NO_3)_3.9H_2O$; 32.1 g $Zn(NO_3)_2.6H_2O$; 1.5 g $Ca(NO_3)_2.4H_2O$; 3.0 g $Co(NO_3)_3.6H_2O$ and 1.6 g $Mg(NO_3)_2.6H_2O$ in deionized water then mixing their solution to form the precursors. The volume of the water solution was 500 ml. The precursor solution and 20 wt. % $NH_4OH$ solution were added separately and simultaneously to 100 ml deionized water by drop wise addition in stoichiometric amounts through two parallel lines. The pH of the solution was kept at 9.4 by regulating the rate of $NH_4OH$ added. The amount of the $NH_4OH$ solution needed for complete precipitation was 162 ml.

After precipitation, the temperature of the precipitate was increased to 75-80° C. After reaching this temperature, the heating was discontinued and the precipitate was allowed to cool to 33° C. At 33° C. the precipitate was filtered and then washed twice with 500 ml of deionized water (1000 ml total). After washing, the precipitate was dried at 120° C. for 4 hours. The precipitate was then calcined at 250° C. for 10 hours and then the calcining temperature was increased to 650° C. for 10 hours. After calcination, the resulting catalyst was cooled, crushed and screened to provide 20-50 mesh size catalyst particles. The final catalyst had 10.10 wt. % Zn, 57.66 wt. % Fe, 0.36 wt. % Ca, 2.58 wt. % Co and 0.20 wt. % Mg.

Approximately 9 g of the formed catalyst was used in the oxidative dehydrogenation of butene to butadiene in a fixed bed reactor at a space velocity 342 $h^{-1}$, an $O_2$/butene molar ratio of 0.65 and $H_2O/C_4$ ratio of 10. The molar feed composition was kept constant at $C_4H_8:CH_4:O_2:H_2O=1:1:0.65:10$. The reactor was initially heated in nitrogen flow to a temperature of 330° C. before the reactant components were added. During the reaction, the catalyst bed temperature was maintained at 347° C. The results are presented in Table 4 below. As can be seen, the catalyst provided both a high conversion and selectivity and at lower reaction temperatures, as compared to the catalysts of Examples 1-3. Lower reaction temperatures typically increase the usable life of the catalyst.

TABLE 4

| Time on Stream (Days) | Butene Conversion, (%) | Selectivity to Butadiene (%) | Catalyst Bed Temperature (° C.) |
|---|---|---|---|
| 1 | 63.2 | 92.7 | 347 |
| 2 | 60.1 | 92.5 | 347 |

Example 5

A Zn—Fe—Co—Mg—Ca modified catalyst was prepared by a two-step simultaneous stoichiometric precipitation process. The stoichiometric precipitation of Ca, Co and Mg was conducted after completing the precipitation of Zn and Fe. This method eliminates the effect of the other salts on the precipitation of the Zn due to the very basic properties of the salts. Because of differences in the precipitation properties of the salts that may affect the precipitation of Zn, these salts were precipitated in a later step. $Fe^{+3}$ is readily precipitated by $NH_4OH$ and is therefore affected less by the other salts compared to Zn. The catalyst was prepared by using 99.8 g $Fe(NO_3)_3.9H_2O$; 32.1 g $Zn(NO_3)_2.6H_2O$; 1.5 g $Ca(NO_3)_2.4H_2O$; 3.0 g $Co(NO_3)_3.6H_2O$ and 1.6 g $Mg(NO_3)_2$. The Zn and Fe salts were dissolved first in 500 ml. The solution of 99.8 g $Fe(NO_3)_3.9H_2O+32.1$ g $Zn(NO_3)_2.6H_2O$ and 20 wt. % $NH_4OH$ solution was simultaneously added by drop wise addition in two parallel lines to 100 ml of deionized water for stoichiometric precipitation at a constant pH between 9.4-9.5. The pH was controlled by controlling the rate of $NH_4OH$ addition. The amount of the $NH_4OH$ solution needed for complete precipitation of Zn and Fe was 162 ml. After completion of the Fe+Zn precipitation, the second step of precipitation started where the mixture of Ca+Mg+Co were simultaneously precipitated with $NH_4OH$ as an addition to the previous precipitate. The pH was also maintained between 9.4-9.5 and controlled by controlling the rate of $NH_4OH$ addition. The amount of the 20 wt. % $NH_4OH$ solution needed for complete precipitation of Ca, Co and Mg was 20 ml.

After precipitation of all the components, the temperature of the precipitate was increased to 75-80° C. After reaching this temperature, the heating was discontinued and the precipitate was allowed to cool to 33° C. At 33° C. the precipitate was filtered and then washed twice with 500 ml of deionized water (1000 ml total). After washing, the precipitate was dried at 120° C. for 4 hours. The precipitate was calcined at 250° C. for 10 hours and then the calcining temperature was increased to 650° C. for 10 hours. After calcination, the resulting catalyst was cooled, crushed and screened to provide 20-50 mesh size catalyst particles. The final catalyst had 12.99 wt. % Zn, 55.87 wt. % Fe, 0.28 wt. % Ca, 2.60 wt. % Co and 0.10 wt. % Mg.

Approximately 9 g of the catalyst was used in the oxidative dehydrogenation of butene to butadiene in a fixed bed reactor at a space velocity 342 $h^{-1}$, an $O_2$/butene molar ratio of 0.65 and $H_2O/C_4$ ratio of 10. The molar feed composition was kept constant at $C_4H_8:CH_4:O_2:H_2O=1:1:0.65:10$. The reactor was initially heated in nitrogen flow to a temperature of 330° C. before the reactant components were added. During the reaction, the catalyst bed temperature was maintained at 344° C. The results are presented in Table 5 below. As can be seen, the catalyst provided both a high conversion and selectivity and at lower reaction temperatures, as compared to the catalysts of Examples 1-3. Lower reaction temperatures typically increase the usable life of the catalyst.

TABLE 5

| Time on Stream (Days) | Butene Conversion, (%) | Selectivity to Butadiene (%) | Catalyst Bed Temperature (° C.) |
|---|---|---|---|
| 1 | 68.0 | 93.9 | 344 |
| 2 | 68.6 | 93.0 | 344 |
| 4 | 68.5 | 93.0 | 344 |

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of forming a catalyst for oxidative dehydrogenation of organic compounds comprising:
forming a reaction solution by simultaneously adding to an aqueous liquid separate streams of (1) and (2), wherein (1) is a base and (2) is catalyst precursor components comprised of $Fe^{+3}$ and $Zn^{+2}$ cations in solution and at least one other modifier element cation in solution that has a standard reduction potential of from greater than about $-2.87\ E°\ (V)$ to less than about $-0.036\ E°\ (V)$ with a valence of +2, and wherein (1) and (2) are simultaneously combined in amounts to maintain the pH of the reaction solution at a pH of from 8.5 to 9.5;
allowing the catalyst precursor components to react and precipitate out of solution; and
calcining the precipitate to form a modified zinc ferrite catalyst compound.

2. The method of claim 1, wherein:
the base is selected from at least one of ammonium hydroxide, ammonium carbonate, ammonium bicarbonate, and sodium hydroxide.

3. The method of claim 1, wherein:
the catalyst is formed without any catalyst template.

4. The method of claim 1, wherein:
the modifier elements are used in amounts of from 0.1 to 3% by weight of the catalyst.

5. The method of claim 1, wherein:
the at least one other modifier element is selected from at least one of Mn, Mo, V, Bi, Sb, Ce, La, Sm, Ca, Mg, Co, Sn, Al, Ba, and Sr.

6. The method of claim 1, wherein:
the at least one other modifier element is selected from at least one of La, Mn, Sn, In, Al, Mg, and Co.

7. The method of claim 1, wherein:
the at least one other modifier element is selected from at least one of Mg and Co.

8. The method of claim 1, wherein:
the catalyst precursor components of $Fe^{+3}$ and $Zn^{+2}$ cations in solution are added first to the aqueous liquid without the at least one other modifier element cation in solution so that Fe and Zn components are precipitated out of solution first, followed by adding the at least one other modifier element cation in solution so the at least one other modifier element components are precipitated out of solution.

9. The method of claim 1, wherein:
the pH of the reaction solution is maintained at a pH of from 9.4 to 9.5.

10. The method of claim 1, wherein;
the reaction solution contains a catalyst template.

11. The method of claim 1, wherein:
the catalyst precursor components of $Fe^{+3}$ and $Zn^{+2}$ cations and the at least one other modifier element cation are added to the aqueous liquid in the same solution.

12. A method of forming a catalyst for oxidative dehydrogenation of organic compounds comprising:
forming a reaction solution by simultaneously adding to an aqueous liquid separate streams of (1) and (2), wherein (1) is a base and (2) is catalyst precursor components comprised of $Fe^{+3}$ and $Zn^{+2}$ cations in solution and at least one other non-chromium modifier element cation in solution that has a standard reduction potential of from greater than about $-2.87\ E°\ (V)$ to less than about $-0.036\ E°\ (V)$ with a valence of +2, and wherein (1) and (2) are simultaneously combined in amounts to maintain the pH of the reaction solution at a pH of from 9.4 to 9.5;
allowing the catalyst precursor components to react and precipitate out of solution;
collecting and washing the precipitate;
drying the washed precipitate; and
calcining the precipitate to form a modified zinc ferrite catalyst compound.

13. The method of claim 12, wherein:
the base is selected from at least one of ammonium hydroxide, ammonium carbonate, ammonium bicarbonate, and sodium hydroxide.

14. The method of claim 12, wherein:
the catalyst is formed without any catalyst template.

15. The method of claim 12, wherein:
the modifier elements are used in amounts of from 0.1 to 3% by weight of the catalyst.

16. The method of claim 12, wherein:
the at least one other modifier element is selected from at least one of Mn, Mo, V, Bi, Sb, Ce, La, Sm, Ca, Mg, Co, Sn, Al, Ba, and Sr.

17. The method of claim 12, wherein:
the at least one other modifier element is selected from at least one of La, Mn, Sn, In, Al, Mg, and Co.

18. The method of claim 12, wherein:
the at least one other modifier element is selected from at least one of Mg and Co.

19. The method of claim 12, wherein:
the catalyst precursor components of $Fe^{+3}$ and $Zn^{+2}$ cations in solution are added first to the aqueous liquid without the at least one other modifier element cation in solution so that Fe and Zn components are precipitated out of solution first, followed by adding the at least one other modifier element cation in solution so the at least one other modifier element components are precipitated out of solution.

20. The method of claim 12, wherein:
the catalyst precursor components of $Fe^{+3}$ and $Zn^{+2}$ cations and the at least one other modifier element cation are added to the aqueous liquid in the same solution.

* * * * *